United States Patent
Katashkina et al.

(10) Patent No.: US 7,604,979 B2
(45) Date of Patent: Oct. 20, 2009

(54) METHOD FOR PRODUCING AN L-AMINO ACID USING A BACTERIUM WITH AN OPTIMIZED LEVEL OF GENE EXPRESSION

(75) Inventors: Joanna Yosifovna Katashkina, Moscow (RU); Maria Grigorievna Lunts, Moscow (RU); Vera Georgievna Doroshenko, Moscow (RU); Svetlana Aleksandrovna Fomina, Moscow (RU); Aleksandra Yurievna Skorokhodova, Moscow (RU); Lirina Valerievna Ivanovskaya, Moscow (RU); Sergei Vladimirovich Mashko, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 314 days.

(21) Appl. No.: 11/222,983

(22) Filed: Sep. 12, 2005

(65) Prior Publication Data
US 2006/0063240 A1 Mar. 23, 2006

Related U.S. Application Data

(63) Continuation of application No. PCT/JP2004/003377, filed on Mar. 12, 2004.

(30) Foreign Application Priority Data

Mar. 12, 2003 (RU) ............... 2003106551
Dec. 18, 2003 (RU) ............... 2003136412

(51) Int. Cl.
*C12N 1/20* (2006.01)
*C12N 15/11* (2006.01)

(52) U.S. Cl. ................... 435/252.1; 536/23.1

(58) Field of Classification Search .............. None
See application file for complete search history.

(56) References Cited

U.S. PATENT DOCUMENTS 5,378,616 A 1/1995 Tujimoto et al.
5,573,945 A 11/1996 Ono et al.
5,908,768 A 6/1999 Ono et al.
6,960,455 B2 11/2005 Livshits et al.
7,332,309 B2 * 2/2008 Rieping ..................... 435/115
2003/0148473 A1 8/2003 Livshits et al.
2004/0229320 A1 11/2004 Stoynova et al.
2005/0191684 A1 9/2005 Zimenkov et al.

FOREIGN PATENT DOCUMENTS

WO      WO 98/07846      2/1998

OTHER PUBLICATIONS

Official Communication from European Patent App. No. 04720229.6 (Dec. 18, 2007).
Datsenko, et al., "One-step inactivation of chromosomal genes in *Escherichia coli* K-12 using PCR products," PNAS 2000;97(12):6640-6645.
Horwitz, M. S. Z., et al., "Promoters selected from random DNA sequences," Proc. Natl. Acad. Sci. USA 1986;83:7405-7409.
Solem, C., et al., "Modulation of Gene Expression Made Easy," Appl. Environment. Microbiol. 2002;68(5):2397-2403.
International Search Report for PCT Application No. PCT/JP2004/003377 (Sep. 10, 2004).
Written Opinion of the International Searching Authority for PCT Application No. PCT/JP2004/003377 (Sep. 29, 2004).

* cited by examiner

*Primary Examiner*—Nancy Vogel
*Assistant Examiner*—Michele K. Joike
(74) *Attorney, Agent, or Firm*—Shelly Guest Cermak; Cermak Kenealy Vaidya & Nakajima LLP

(57) ABSTRACT

A method is provided for obtaining an L-amino acid or nucleic acid-producing bacterium belonging to the genus *Escherichia* with an optimized level of expression of the gene which influences the distribution of carbon flow, such as the sucAB genes, comprising introducing into the chromosome of the bacterium a set of in vitro constructed DNA fragments which contain regulatory elements for gene expression instead of the native elements of the regulatory region of the gene, and selecting the colonies with increased L-amino acid productivity. Also, a method is provided for producing an L-amino acid, such as L-glutamic acid, L-proline, L-arginine, L-glutamine, L-leucine, using the bacterium with an optimized level of expression of the sucAB gene.

3 Claims, 1 Drawing Sheet

**1. *In vitro* construction of the PCR-amplified DNA fragment used for the substitution of the native upstream region of the sucAB genes.**

**2. Red-driven integration of the hybrid regulatory element carrying the synthetic Ptac* promoter and SDlacZ.**

Before integration:

After integration:

METHOD FOR PRODUCING AN L-AMINO ACID USING A BACTERIUM WITH AN OPTIMIZED LEVEL OF GENE EXPRESSION

This application is a continuation under 35 U.S.C. §120 of PCT/JP2004/003377 filed Mar. 12, 2004, the entirety of which is incorporated by reference.

BACKGROUND OF THE INVENTION

1. Field of the Invention

The present invention relates to a method for obtaining a bacterium having an optimized level of gene expression, which is useful for amino acid or nucleic acid production, and a method for producing an L-amino acid or nucleic acid using the bacterium.

2. Brief Description of the Related Art

Traditionally, enhancing the activity of gene products involved in biosynthetic pathways of L-amino acids or nucleic acids was a common method used to increase L-amino acid or nucleic acid production. This was often accomplished by creating mutants resistant to target compounds or analogs, enhancing the expression of the biosynthetic genes, eliminating sensitivity of biosynthetic enzymes to feedback inhibition by products and intermediates of the biosynthesis, and creating bacterial strains deficient in genes which encode enzymes using the precursors of the target compound for other pathways, or creating bacterial strains deficient in genes which are responsible for the degradation of the target compound.

These manipulations usually lead to the creation of strains which cannot grow, or grow only at a significantly reduced rate, or require additional nutrients such as amino acids. For example, enhancement of expression of some genes may become excessive and could lead to significant inhibition of bacterial growth and, as a result, lower the ability of the bacterium to produce the target compound.

It is known that microorganisms belonging to the genus Escherichia which are deficient in or possess a decreased level of α-ketoglutarate dehydrogenase, have the ability to produce L-glutamic acid (U.S. Pat. Nos. 5,573,945 and 5,908,768). But these mutants cannot grow or are only able to grow at significantly reduced rates in glucose minimal media under aerobic conditions. Addition of succinic acid or lysine supplemented with methionine is necessary to restore growth. Therefore, the selection of an optimal expression level for α-ketoglutarate dehydrogenase is necessary for the bacterium to acquire the abilities to produce glutamic acid and to grow in a medium containing no additional supplements, such as succinic acid, lysine, or methionine.

On the other hand, it is known that genes encoding succinate dehydrogenase (sdhCDAB genes) as well as genes encoding α-ketoglutarate dehydrogenase (sucAB genes) and succinyl-CoA synthase (sucCD genes) form a cluster containing two promoters in the chromosome of E. coli: $P_{sdh}$-sdhCDAB-$P_{suc}$-sucAB-sucCD (Park, S. J., Chao, G., and Gunsalus, R. P., J. Bact. 179, 4138-4142, 1997; Cunningham, L., and Guest, G. R., Microbiology, 144, 2113-2123, 1998). The main promoter for this operon structure is the regulatory region located upstream of the sdhC gene, $P_{sdh}$. The weaker $P_{suc}$-promoter recognized by E. coli RNA polymerase in the complex with $\sigma^{38}$ provides an additional low constitutive level of sucABCD gene expression. The activity of the later promoter has been relatively unaffected by the growth substrate. In addition, the effects of anaerobiosis and arcA or fnr mutations are relatively small. ArcA protein is a negative response regulator of genes in aerobic pathways, and Fnr (fumarate and nitrate reduction) protein is involved in transcriptional regulation of aerobic, anaerobic respiration and osmotic balance. Among potential regulators tested, IHF protein (integration host factor—product of himA gene) might play the major role in repressing $P_{suc}$ activity. ArcA and Fnr proteins interact with $P_{sdh}$ promoter and IHF protein interacts with weaker $P_{suc}$ promoter.

Obtaining a library of synthetic promoters for Lactococcus lactis with different strengths has been described (Jensen P. R., and Hammer K., Appl. Environ. Microbiol., 1998, 64, No. 1. 82-87 Biotechnol. Bioeng., 1998, 58, 2-3, 191-5). The library consists of 38 oligonucleotides having randomized spacers between the consensus sequences in the positions from −35 to −15. To evaluate the strength of the resulting promoters, oligonucleotides from the library were cloned into the expression vector pAK80, which contains β-galactosidase. It was shown that the majority of artificial promoters were very weak (below 500) and only three of them had a strength of about 2000 relative units. But no practical application for this library of synthetic promoters was disclosed.

A method for producing coryneform bacteria having an improved amino acid- or nucleic acid-productivity by introducing a mutation into a promoter sequence of amino acid- or nucleic acid-biosynthesizing genes is disclosed in the European Patent Application EP1033407A1. Up to 8 different variants of mutant promoters were used for each of the following genes: glutamate dehydrogenase (gdh) gene, citrate synthase (gltA) gene, isocitrate dehydrogenase(icd) gene, pyruvate dehydrogenase (pdhA) gene, and argininosuccinate synthase (argG) gene. The disadvantage of the technique described in European application EP1033407A1 is that each of described mutants was prepared separately, that is one by one. Also, increasing L-amino acid production in all cases disclosed in this patent application was achieved by increasing the activity of certain enzymes using a limited amount of different promoters for the gene encoding the enzyme. This approach is within the mainstream of work focused on preparing L-amino acid or nucleic-acid producing bacteria, and does not pertain to optimization or fine-tuning of promoter activity of genes essential for production of L-amino acids or nucleic acids.

There have been no reports describing the optimization of gene expression for metabolite production by fermentation of a bacterium which has been modified to have an optimized level of target gene expression.

SUMMARY OF THE INVENTION

It is an object of the present invention to provide a method for obtaining a bacterium having an optimized level of expression for a target gene encoding a protein which influences the distribution of carbon or nitrogen fluxes in said bacterium, comprising the following steps: (1) introducing into the chromosome of said bacterium a set of in vitro-constructed DNA fragments containing regulatory elements for said target gene expression in place of the native regulatory elements of said target gene, and (2) selecting the bacterium with the desired phenotype.

It is a further object of the present invention to provide an L-amino acid-producing bacterium having an optimized level of expression of the gene encoding a protein which influences L-amino acid production, wherein said bacterium is obtained by the method as described above.

It is a further object of the present invention to provide a method for producing an L-amino acid which comprises the following steps (1) cultivating the bacterium as described above in a culture medium to cause accumulation of L-amino acid in the culture medium, and (2) collecting L-amino acid from the culture medium.

DESCRIPTION OF THE PREFERRED EMBODIMENTS

Figure 1:
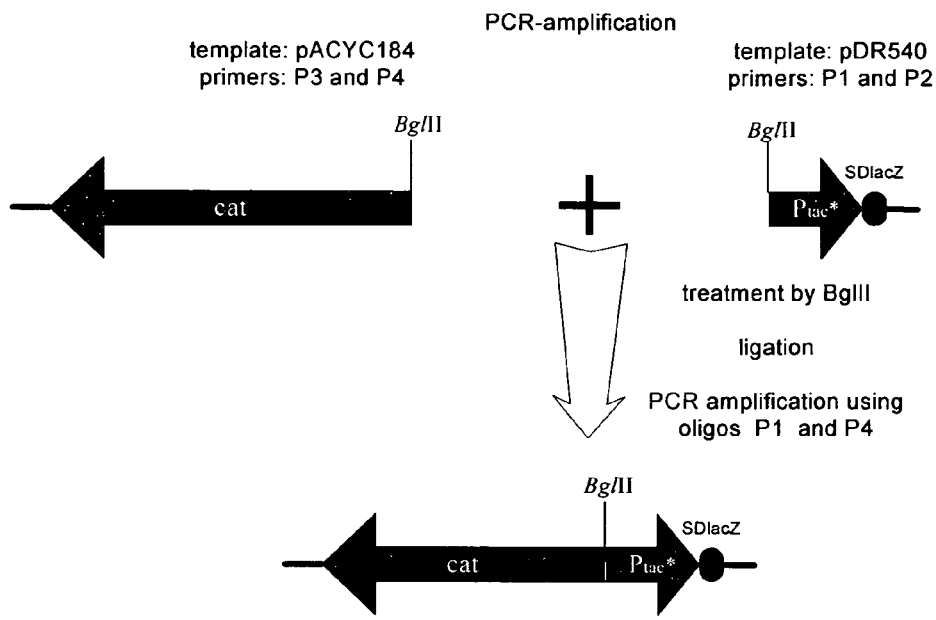
FIG. 1 shows a scheme for construction of the artificial DNA fragment containing the hybrid regulatory element with the randomized region and the chloramphenicol resistance gene (cat), and Red-driven integration of the hybrid regulatory element.
Figure 1:
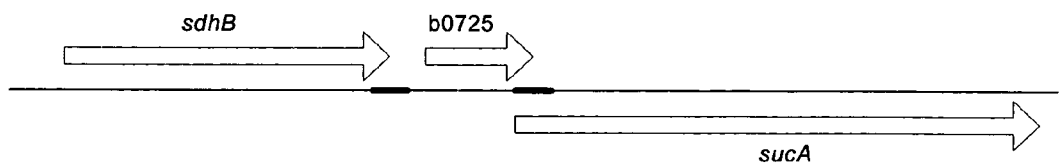
Figure 1:
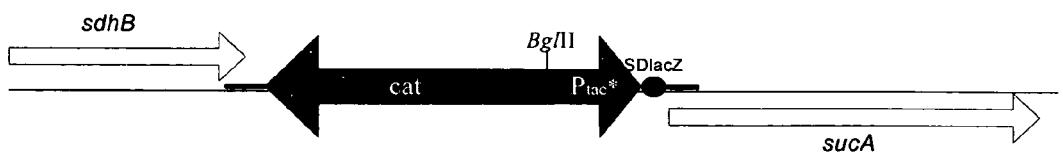

The present invention provides a simple and straightforward one-step method for obtaining an L-amino acid-producing bacterium having an optimized level of expression of the gene which influences distribution of carbon or nitrogen fluxes in the bacterium and, accordingly, influences production of L-amino acids or nucleic acids. The present invention further provides a bacterium with an optimized level of expression of the gene which influences production of L-amino acids or nucleic acids by increasing said production, and provides a method for producing L-amino acids, such as glutamic acid or an L-amino acid derived from L-glutamic acid, such as L-arginine, L-proline, L-glutamine, and also L-leucine; a method for producing L-amino acids such as L-lysine, L-isoleucine, L-valine, L-histidine, L-aspartic acid, L-alanine, L-tyrosine and L-phenylalanine, biosynthesis of which requires L-glutamic acid as a donor of amino group; and a method for producing nucleic acids.

The present invention was achieved by substituting the native promoter of the target gene with a "randomized" promoter-like sequence directly into the bacterial chromosome. This idea is based on the -fact that mutants with modified "–35" regions of the promoters recognized by the complex of $E.\ coli$ RNA polymerase with $\sigma^{70}$ significantly can change the efficiency of transcription initiation. Therefore, among the promoters created with the initial random promoter-like sequence, promoters with different strengths are obtained and the optimal constructions are selected due to direct evaluation of the productivity (and maybe other physiological characteristics) of the plasmid less strains.

This general approach has been exploited for fine-tuning of expression of the sucAB genes in a model recombinant $E.\ coli$ strain to increase the L-glutamic acid production level. Achieving optimization rather than maximization of gene or operon expression is an actual problem in construction of different bacterial strains able to produce biologically active metabolites, especially in cases where the low level of expression of the target gene or genes is not enough for achieving the final object, and, on the other hand, overexpression of the corresponding gene or genes could result in not only a neutral, but also a negative effect. Moreover, the desired level of this key-gene activity is unknown. Fine-tuning is extremely desirable for providing optimization and, therefore, a lot of variants must be tested. A traditional approach for conducting this sort of fine-tuning includes molecular cloning of the target gene into recombinant plasmids and placing it under the control of different promoters, followed by the evaluation of the resulting recombinant strains. After selection of the best variants, a lot of additional work is necessary if a plasmidless improved strain-producer is desired.

1. Method of the Present Invention

A method of the present invention includes obtaining an L-amino acid-producing bacterium with an optimized level of expression of a target gene which influences distribution of carbon flux in the bacterium and, as a result, influences L-amino acid production, which has the following steps: (1) introducing into the bacterial chromosome a set of in vitro-constructed DNA fragments containing regulatory elements for said target gene expression in place of the native regulatory elements of said target gene, and (2) selecting the bacterium with the desired phenotype.

The term "expression" as used herein means the production of the protein product encoded by a gene.

The term "optimized level of expression" means expression of the targeted gene or several genes that results in the bacterium having the desired phenotype.

The term "desired phenotype" includes one or several characteristics of the bacterium, which are the objects for improvement. Preferably, it could be the ability of the bacterium to produce an L-amino acid in greater amounts then the parental strain; it could also be the ability to grow in minimal medium which does not contain additives usually used to complement an auxotrophy or other requirements for growth factors, or a combination thereof.

The term "gene encoding a protein which influences distribution of carbon or nitrogen fluxes" means the gene encoding a protein which is involved in carbon or nitrogen metabolic pathways. Examples of such genes include, but are not limited to glycolysis or nitrogen assimilation genes, pentose cycle genes, TCA cycle genes, and so forth. More specifically, examples include, but are not limited to glutamate dehydrogenase, glutamine synthetase, glutamate synthase, isocitrate dehydrogenase, aconitate hydratase, citrate synthase, phosphoenolpyruvate carboxylase, pyruvate dehydrogenase, pyruvate kinase, phosphoenolpyruvate synthase, enolase, phosphoglyceromutase, phosphoglycerate kinase, glyceraldehyde-3-phosphate dehydrogenase, triose phosphate isomerase, fructose bisphosphate aldolase, phosphofructokinase, glucose phosphate isomerase, glutamine-oxoglutarate aminotransferase, isopropylmalate synthase, and so forth. Bacterial genes involved in biosynthetic pathways of L-amino acids, nucleic acids and their precursors may also be included.

The phrase "a set of in vitro-constructed DNA fragments" means a mixture of newly synthesized DNA fragments or a mixture of known DNA fragments obtained from native or mutated microorganisms, DNA libraries, GenBank etc. The set of DNA fragments may be formed by direct mixing of newly synthesized DNA fragments with known sequences, DNA fragments obtained from different sources mentioned above, or DNA fragments obtained by chemical synthesis and having the region containing the randomized sequence.

The phrase "randomized sequence" means that during standard chemical synthesis of a DNA fragment, random nucleotides (usually designated as N, where N is adenine, guanine, cytosine, or thymine) are introduced into certain positions of the DNA fragment or some region of the DNA fragment having random nucleotide sequences, respectively. The DNA fragments contain sequences called "regulatory elements."

The phrase "regulatory elements" refers to nucleotide sequences located upstream, within and/or downstream of a coding region which control transcription and/or expression of the coding region in conjunction with the protein biosynthetic apparatus of the cell. The phrase is usually used when designating promoters, ribosome binding sites (RBS), operators, or other elements of a genome, and which influence gene expression levels.

The mixture of said DNA fragments containing regulatory elements is introduced into the chromosome of the bacterium in place of the native regulatory element resulting in a population of bacterial cells with the different levels of expression of the target gene. Selection of the bacterium with a desired phenotype may be performed by direct evaluation of the amount of L-amino acid produced in standard minimal medium or other methods suitable for estimation of the characteristics essential to the desired phenotype.

The phrase "L-amino acid-producing bacterium" as used herein means a bacterium which is able to cause accumulation of a target L-amino acid in culture medium in an amount larger than a wild-type or parental strain, and preferably means that the microorganism is able to cause accumulation in a medium of an amount not less than 0.5 g/L, more preferably not less than 1.0 g/L of target L-amino acid.

The phrase "a bacterium belonging to the genus *Escherichia*" means that the bacterium is classified as the genus *Escherichia* according to the classification known to a person skilled in the art of microbiology. An example of a microorganism belonging to the genus *Escherichia* used in the present invention include, but are not limited to, *Escherichia coli* (*E. coli*).

Determination of the level of enzyme activity and selection of optimal regulatory element sequences for certain conditions requires an elevated skill in the art; and selection of regulatory element sequences based on scientific guess or insight may not lead to the desired or optimal result. Furthermore, preparation of even a limited amount of mutants with varying levels of enzyme activity is complicated and time-consuming because such mutants are traditionally prepared one-by-one. To the contrary, the method of the present invention advantageously provides a simple and straightforward one-step process of artificial or native DNA fragment integration into the chromosome generating a population of bacterial cells with a wide spectrum of expression levels for the target gene. For example, randomization of 4 nucleotides in a certain region of the chemically synthesized regulatory element provides $4^4$, or 256 theoretically possible variants of the region.

Furthermore, it is typical to evaluate the activity of a target enzyme by introducing a gene encoding the enzyme into a plasmid hosted by a bacterium. But expression level of the gene integrated into the bacterial chromosome and expression level of the same gene introduced into a plasmid hosted by a bacterium may not be the same. So another advantage of the method of the present invention is that the method allows for evaluation and selection of the bacterium under optimal conditions for expression of the target gene, followed by direct use of the bacterium for L-amino acid production without any additional manipulation.

Methods for preparation of plasmid DNA, digestion and ligation of DNA, transformation, selection of an oligonucleotide as a primer, and the like are well known to one skilled in the art. These methods are described, for instance, in Sambrook, J., Fritsch, E. F., and Maniatis. T., "Molecular Cloning A Laboratory Manual, Second Edition"; Cold Spring Harbor Laboratory Press (1989).

2. Bacterium of the Present Invention

A bacterium of the present invention is an L-amino acid-producing bacterium having an optimized level of expression of the gene which influences L-amino acid production. Such a bacterium may be obtained by the method of the present invention.

More specifically, the bacterium of the present invention is a bacterium producing an L-amino acid derived from L-glutamic acid, and having an optimized level of expression of the gene which influences L-glutamic acid production. L-arginine, L-proline, and L-glutamine are all derived from L-glutamic acid. Also, the bacterium of the present invention includes an L-glutamic acid-producing bacterium having an optimized level of expression of the gene which influences L-glutamic acid production. Moreover, L-glutamic acid plays a significant role in the biosynthesis of L-leucine, L-lysine, L-isoleucine, L-valine, L-histidine, L-aspartatic acid, L-alanine, L-tyrosine, and L-phenylalanine as a donor of an amino group. Therefore, improvement in nitrogen donation for the gene encoded aminotransferase is effective in production of other amino acids such as L-leucine, L-lysine, L-isoleucine, L-valine, L-histidine, L-aspartic acid, L-alanine, L-tyrosine, and L-phenylalanine. Thus, the bacterium of the present invention includes bacterium producing L-arginine, L-proline, L-glutamine, L-leucine, and a bacterium producing L-lysine, L-isoleucine, L-valine, L-histidine, L-aspartic acid, L-alanine, L-tyrosine, or L-phenylalanine.

The particular embodiment of the present invention is the L-glutamic acid-producing *E. coli* strain 702ilvA (VKPM B-8012) (EP 1772433A1) containing the recombinant plasmid pAYCTER1-cpg, which is further modified to have an optimized level of expression of the sucAB genes. Plasmid pAYCTER1-cpg is the derivative of RSF1010 replicon having native genes encoding citrate synthase (gltA gene), phosphoenolpyruvate carboxylase (ppc gene), glutamate dehydrogenase (gdhA gene) and proBA-operon (glutamate-5-semialdehyde dehydrogenase, glutamate 5-kinase) cloned from the *E. coli* strain K-12 by standard methods. Optimization of sucAB gene expression is performed by the method of the present invention. The recombinant strain 702 ilvA [pAYCTER1-cpg] is deficient in threonine deaminase, requires L-isoleucine for growth, and is able to produce L-proline and L-glutamic acid during cultivation.

Bacteria belonging to the genus *Escherichia* which are able to produce L-glutamic acid and could be an object for optimization of gene expression are exemplified by the following *E. coli* strains: strains which are resistance to an aspartic acid antimetabolite and are deficient in alpha-ketoglutaric acid dehydrogenase activity, such as AF13199 (FERM BP-5807) (U.S. Pat. No. 5,908,768), or strain FERM P-12379 additionally having low L-glutamic acid decomposing ability (U.S. Pat. No. 5,393,671); *E. coli* strain AJ13138 (FERM BP-5565) (U.S. Pat. No. 6,110,714), and the like. L-glutamic acid-producing ability can be further imparted or enhanced by, for example, introducing a DNA that codes for an enzyme including, but not limited to glutamate dehydrogenase (Japanese Patent Application Laid-open (Kokai) 61-268185/1986), glutamine synthetase, glutamate synthase, isocitrate dehydrogenase (Japanese Patent Application Laid-open (Kokai) Nos. 62-166890/1987 and 63-214189/1988), aconitate hydratase (Japanese Patent Application Laid-open (Kokai) No. 62-294086/1987), citrate synthase (Japanese Patent Application Laid-open (Kokai) Nos. 62-20 585/1987 and 63-119688/1988), phosphoenolpyruvate carboxylase (Japanese Patent Application Laid-open (Kokai) Nos. 60-87788/1985 and 62-55089/1987), pyruvate dehydrogenase, pyruvate kinase, phosphoenolpyruvate synthase, enolase, phosphoglyceromutase, phosphoglycerate kinase, glyceraldehyde-3-phosphate dehydrogenase, triose phosphate isomerase, fructose bisphosphate aldolase, phosphofructokinase (Japanese Patent Application Laid-open (Kokai) No. 63-1 02692/1 988), glucose phosphate isomerase, glutamine-oxoglutarate aminotransferase (W099/07853), and so forth. Furthermore, the bacterium of the present invention may be altered so that it is deficient in activity of an enzyme that catalyzes a reaction which generates a compound other than L-glutamic acid by branching off from the biosynthetic pathway of L-glutamic acid. This enzyme that catalyzes the reaction for generating the compound other than L-glutamic acid by branching off from the biosynthetic pathway L-glutamic acid includes, but is not limited to α-ketoglutarate dehydrogenase, isocitrate lyase, phosphate acetyltransferase, acetate kinase, acetohydroxy acid synthase, acetolactate synthase, formate acetyltransferase, lactate dehydrogenase, glutamate decarboxylase, 1-pyrroline dehydrogenase, and so forth.

Also, it is possible to use the L-leucine-producing bacteria belonging to the genus *Escherichia* such as *E. coli* strains H-9068 (ATCC 21530), H-9070 (FERM BP-4704) and H-9072 (FERM BP-4706) resistant to 4-azaleucine or 5,5,5-trifluoroleucine (U.S. Pat. No. 5,744,331), *E. coli* strains in which feedback inhibition of isopropylmalate synthase by L-leucine is desensitized (European patent EP1067191), *E. coli* strain AJ11478 resistant to β-2-thienylalanine and β-hydroxyleucine (U.S. Pat. No. 5,763,231), *E. coli* strain 57 resistant to L-leucine (VKPM B-7386, Russian patent No. 2140450), and the like.

The strategy described above for L-glutamic acid and L-leucine could be used to obtain a bacterium which produces other known L-amino acids.

3. Method for Producing L-Amino Acid

The method for producing the L-amino acid is a method which includes the steps of cultivating the bacterium of the present invention in a culture medium to cause accumulation of the L-amino acid in the medium, and collecting the L-amino acid from the medium. More specifically, the method for producing the L-amino acid includes a method for producing L-glutamic acid which includes the steps of cultivating the bacterium of the present invention in a culture medium to cause accumulation of the L-glutamic acid in the medium, and collecting the L-glutamic acid from the medium. Also the method for producing the L-amino acid includes a method for producing L-glutamine, L-arginine, L-proline or L-leucine, which includes the steps of cultivating the bacterium of the present invention in a culture medium to cause accumulation of the L-glutamine, L-arginine, L-proline or L-leucine in the medium, and collecting the L-glutamine, L-arginine, L-proline, or L-leucine from the medium.

In the present invention, the cultivation, the collection, and purification of L-amino acid from the medium and the like may be performed in a manner similar to conventional fermentation methods wherein an amino acid is produced using a bacterium.

The medium used for culture may be either a synthetic or natural medium, so long as the medium includes a carbon source, a nitrogen source, minerals and, if necessary, appropriate amounts of nutrients which the bacterium may require for growth. The carbon source may include various carbohydrates such as glucose and sucrose, and various organic acids. Depending on the assimilation mode of the chosen microorganism, alcohol including ethanol and glycerol may be used. The nitrogen source may be various ammonium salts such as ammonia and ammonium sulfate, other nitrogen compounds such as amines, a natural nitrogen source such as peptone, soybean-hydrolysate, and digested fermentative microorganism. Minerals may include potassium monophosphate, magnesium sulfate, sodium chloride, ferrous sulfate, manganese sulfate, calcium chloride, and the like. Vitamins may include thiamine, yeast extract, and the like.

Preferably, the cultivation is performed under aerobic conditions such as a shaking culture or a stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation period leads to accumulation of the target L-amino acid in the liquid medium.

After cultivation, solids such as cells can be removed from the liquid medium by centrifugation or membrane filtration, and the L-amino acid can be collected and purified by ion-exchange, concentration, and crystallization methods.

EXAMPLES

The present invention will be more concretely explained below with reference to the following non-limiting examples.

Example 1

Substitution of the Native Upstream Region of sucAB-genes on the *E. coli* Chromosome with a Hybrid Regulatory Element having the Synthetic $P_{tac}$*-promoter and $SD_{lacZ}$ A modified $P_{tac}$*-promoter linked to the Shine-Dalgarno sequence (SD sequence) from the lacZ gene derived from *E. coli* was integrated upstream of the sucAB coding region into the chromosome of the *E. coli* strain 702ilvA[pAYCTER1-cpg] in place of the native region by the method described by Datsenko, K. A. and Wanner, B. L. (Proc. Natl. Acad. Sci. USA, 97, 6640-6645, 2000) also called a "Red-mediated recombination" or "Red-driven integration." The modified $P_{tac}$*-promoter contained only the first 11 bp of the 21 bp lactose operator ($O_{lac}$), resulting in an inability to interact with the lactose repressor because of the absence of the nucleotides essential for the specific DNA-protein interactions. In addition, the artificial DNA fragment which contains the chloramphenicol resistance gene ($Cm^R$, or cat) is linked to the 5'-part of the modified $P_{tac}$*-promoter, and provides for further selective integration into the corresponding region of the bacterial chromosome. The scheme for construction of the artificial DNA fragment is depicted in FIG. 1. The nucleotide sequence of the substituted native region located upstream of the sucAB genes is presented in the Sequence listing (SEQ ID NO: 1)

In vitro construction of the above-mentioned artificial DNA fragment having the chloramphenicol resistance gene ($Cm^R$), was executed in the several stages. First, PCR-driven DNA amplification of the $P_{tac}$*-promoter is conducted so that the resulting fragment has the BglII-restriction site upstream (for the convenience of the further gene-engineering constructions, see below), and the SD sequence and ATG-initiating codon of *E. coli* lacZ-gene linked directly to the N-terminal of the sucA coding region is downstream of the resulting promoter-carrying fragment. The commercially available recombinant plasmid, pDR540 (GenBank/EMBL accession number U13847, "Pharmacia", USA) was used as a template for PCR. PCR was conducted using the chemically synthesized oligonucleotides P1 (SEQ ID NO: 2) and P2 (SEQ ID NO: 3) as primers.

In all cases, PCR was conducted using the thermal cycler Perkin-Elmer 2400 GeneAmp PCR System. The reaction mixture had a total volume of 50 µl, and contains 5 µl of 10× PCR-buffer ("Fermentas", Lithuania) and $MgCl_2$ was added up to the final concentration of 1.5 mM, 200 µM each of dNTP, 400 nM each of the exploited primers and 2U Taq-polymerase ("Fermentas", Lithuania). The amount of the template DNA added to the PCR-driven amplification was calculated to result in 0.2 ng of target DNA fragment. The temperature profile for PCR was the following: initial DNA denaturation for 5 min at 95° C. followed by 20 cycles; denaturation at 95° C. for 30 sec, annealing at 55° C. for 30 sec, elongation at 72° C.; the final polymerization for 2 mm at 72° C. The elongation time was chosen according to the manufacturer's instructions for the Taq-polymerase, and depending on the length of the desired amplified DNA fragment. In the example, the elongation time was 1.5 min.

Concurrently, construction of the 2nd objective DNA fragment was conducted. The $Cm^R$ gene was amplified using the commercially available plasmid pACYC184 (GenBank/EMBL accession number X06403, "Fermentas", Lithuania) as the template and the chemically synthesized oligonucleotides P3 (SEQ ID NO: 4) and P4 (SEQ ID NO: 5) as primers. Primer P3 contains the BglII-restriction site and is used to join the previously-obtained DNA fragment having the $P_{tac}$*-promoter. Primer P4 contains 36 nucleotides which are complementary to those located upstream of the regulatory region of sucAB genes in the *E. coli* chromosome necessary for further Red-mediated recombination of the objective fragment into the bacterial chromosome. Primer P4 is depicted in SEQ ID NO: 5 and consists of 57 nucleotides.

The two above-described amplified DNA fragments were treated by BglII-restriction endonuclease and then ligated together using T4 DNA ligase (Maniatis, T., Fritsch, E. F., Sambrook, J.: Molecular Cloning: A Laboratory Manual. $2^{nd}$ edn. Cold Spring Harbor, N.Y.: Cold Spring Harbor Laboratory Press, 1989). Finally, the ligation product was amplified by PCR using primers P1 and P4. The resulting DNA fragment was purified by ethanol and used for electroporation and Red-mediated recombination into the bacterial chromosome of the *E. coli* strain 702ilvA[pAYCTER1-cpg]. *E. coli* strain 702ilvA[pAYCTER1-cpg] is a derivative of the L-glutamic acid-producing *E. coli* strain 702ilvA (VKPM B-8012) (European Patent Application 1772433A1), and also contains the recombinant plasmid pAYCTER1-cpg. Plasmid pAYCTER1-cpg is the derivative of the pAYCTER3 vector, which also contains the native genes encoding citrate synthase (gltA gene), PEP carboxylase (ppc gene), glutamate dehydrogenase (gdhA gene), and proBA-operon cloned from the *E. coli* strain K-12 by standard methods, such as PCR using chromosomal DNA of *E. coli* strain K-12 as a template and primers flanked with restriction sites suitable for further cloning and assembling of PCR products. The pAYCTER3 vector is a derivative of pAYC32, a moderate copy number and a very stable vector constructed on the basis of plasmid RSF1010 (Christoserdov, A. Y., Tsygankov, Y. D., Plasmid, 1986, v. 16, pp. 161-167), which contains the marker for streptomycin resistance. The pAYCTER3 vector was constructed by introduction of the polylinker from pUC19 plasmid and the strong terminator rrnB into pAYC32 plasmid in place of its promoter as follows. First, the polylinker from pUC19 plasmid was obtained by PCR using the primers depicted in SEQ ID No. 6 and No. 7. The resulting PCR product was treated with EcoRI and BglII restriction endonuclease. The terminator rrnB was also obtained by PCR using the primers depicted in SEQ ID No. 8 and No. 9. The resulting PCR product was treated with BglII and BclI restriction endonuclease. Then, these two DNA fragments were ligated into the pAYC32 plasmid which had been previously treated with EcoRI and BclI restriction endonuclease. Thus, the pAYCTER3 plasmid was obtained.

The recombinant plasmid pKD46 (Datsenko, K. A., Wanner, B. L., Proc. Natl. Acad. Sci. USA, 97, 6640-6645, 2000) which contains a thermo-sensitive replicon was used as a donor of the phage λ-derived genes responsible for the Red-mediated recombination system. The cells of strain 702ilvA [pAYCTER1-cpg] were transformed by the pKD46 plasmid according to the standard protocol of Ca-transformation (Maniatis, T., Fritsch, E. F., Sambrook, J.: Molecular Cloning: A Laboratory Manual. $2^{nd}$ edn. Cold Spring Harbor, N.Y.: Cold Spring Harbor Laboratory Press, 1989), followed by selection of objective transformants plates with L-agar (Tryptone, 10 g/l; Yeast extract, 5 g/l; NaCl, 10 g/l; Agar, 1.5%) with addition of ampicillin up to 100 µg/ml. The plates were incubated overnight at 30° C. and the resulting clones were prepared for electrocompetent culture. The cells were grown overnight at 30° C. in liquid LB-medium with the addition of ampicillin (100 µg/ml) and streptomycin (25 µg/ml) diluted to 1:100 by SOB-medium (Yeast extract, 5 g/l; NaCl, 0.5 g/l; Tryptone, 20 g/l; KCl 2.5 mM; $MgCl_2$, 10 mM) with the addition of ampicillin (100 µg/ml), streptomycin (25 µg/ml), and arabinose (10 mM) (arabinose is used for inducing the plasmid encoding genes of phage λ homologous recombination system) and grown at 30° C. to reach the optical density $OD_{600}$=0.8-1.0. The cells from 10 ml of the bacterial culture were washed 3 times by fresh ice-cooled de-ionized water followed by 200 µl of glycerol (10%) and suspended in 40 µl of glycerol (10%). 0.5 µg of the above-described amplified DNA fragment dissolved in 5 µl of de-ionized water was added to the bacterial culture directly before conducting the electroporation procedure. The electroporation was conducted in a bacterial electrotransformation device made by "Bio-Rad" (USA) (No. 165-2098, version 2-89) according to the manufacturer instructions for *E. coli* cells (the pulse-time—4-5 msec, intenseness of the electric field −12.5 kV/sm).

1 ml of SOC-medium (Yeast extract, 5 g/l; Tryptone, 20 g/l; NaCl, 0.5 g/l; KCl, 2.5 mM; $MgCl_2$, 10 mM; Glucose, 20 mM) was added to the cellular suspension immediately after electroporation. Then, the shocked cells were grown using agitation for 2 hours at 37° C. and the integrants were selected on the plates with L-agar containing chloramphenicol (25 µg/ml) and streptomycin (25 µg/ml) after inoculation of the plates overnight at 37° C.

The resulting $Cm^R$ $Sm^R$ clones were replica-plated on the plates with L-agar and grown overnight at 42° C. to eliminate the thermosensitive "helper"-plasmid pKD46. Substitution of the native regulatory region of sucAB-gene in the selected $Ap^S$ $Cm^R$ $Sm^R$-clones of the strain with the in vitro constructed artificial DNA fragment for 702ilvA[pAYCTER1-cpg] was confirmed by PCR.

Example 2

Influence of the $P_{tac}$* Promoter on the Activity of α-ketoglutarate Dehydrogenase and Production of L-glutamic Acid and L-proline A full loop of each strain 702ilvA [pAYCTER1-cpg] and 702ilvA tac* [pAYCTER1-cpg] from the L-agar plate was inoculated into Erlenmeyer flasks containing 75 ml of medium having 10 g/l Tryptone, 5 g/l Yeast extract, 4 g/l NaCl, and 25 μg/ml streptomycin for stabilization of the recombinant plasmid pAYCTER1-cpg, and incubated for 6 h at 37° C. with agitation (rotation speed: 140 rpm). Then, 50 ml of the resulting culture was inoculated into a Jar-fermentor ("Marubishi", Japan). The medium for Jar-fermentation (total volume 500 ml) consists of: 100 g/l glucose, 2 g/l $(NH_4)_2SO_4$, 1 g/l $KH_2PO_4$, 0.4 g/l $MgSO_4.7H_2O$, 0.01 g/l $FeSO_4.7H_2O$, 0.01 g/l $MnSO_4.5H_2O$, 0.2 g/l L-isoleucine, Soybean hydrolysate (0.2 g/l of Total Nitrogen), 0.0004 g/l thiamine.HCl, pH 6.7. The fermentation step is aerated by agitation at 900 rpm at 35° C., and the pH is maintained by the addition of $NH_4OH$ solution.

The amount of L-proline and L-glutamic acid was measured by high performance liquid chromatography (HPLC) under the following conditions: Luna $C_{18}(2)$, 150×3 mm, 5U, temp: 17° C. Eluent: $CH_3CN$—0.8% (v/v), $H_3PO_4$ 0.1% (v/v), $KH_2PO_4$—10 mM, n-$C_8H_{17}SO_3Na$—3 mM. Flow rate—0.4 ml/mm, injection volume 10 μl. Detection at 200 nm. Retention time: glutamic acid—9.3, proline—12.1.

The activity of the α-ketoglutarate dehydrogenase in the resulting strain was determined according to standard procedure (Amarasingham, C. R. & Davis, B. D., J. Biol. Chem. 1965. 240, 3664-3668) following growing the cells under the same conditions as those used for determination of L-proline and L-glutamic acid accumulation. Data are presented in the Table 1.

As seen from the data in Table 1, the substitution of the efficient $P_{tac}$*-promoter for the native $P_{suc}$ results in an increase in the specific α-ketoglutarate dehydrogenase activity up to 3-fold in the cells of the new strain as compared to its progenitor.

However, the new strain almost entirely loses the ability to overproduce L-glutamic acid. Although, L-proline accumulation was slightly increased in the new strain as compared to the non-modified strain, the total conversion of carbon from glucose into the amino acids of the L-glutamic acid family, for example, L-glutamic acid and L-proline, was significantly decreased.

These results clearly show that use of the strong constitutive $P_{tac}$* promoter having consensus "−10" and "−35" regions, results in an up to 3-fold increase of the α-ketoglutarate dehydrogenase activity and, a concurrent decrease in L-glutamic acid overproduction. An increase in the growth rate of the resulting strain as compared to the strain containing the wild-type $P_{suc}$ promoter was also observed (Table 1). These effects are probably due to an increase of the flux through the TCA cycle and, consequently, a higher level of ATP synthesis.

As described in the Description of the Related Art, glutamic acid-producing mutants belonging to the genus Escherichia, which are deficient in or possess a low level of α-ketoglutarate dehydrogenase, cannot grow or are able to grow only at a significantly reduced rate in glucose minimal media under aerobic conditions. Addition of succinic acid or lysine supplemented with methionine is necessary for restoration of growth. Therefore, selection of the optimal expression level for α-ketoglutarate dehydrogenase is necessary for a bacterium to acquire the abilities to produce glutamic acid and to grow on medium containing no additional supplements, such as succinic acid, lysine or methionine.

To obtain the prototrophic strain having a high level of L-glutamic acid overproduction and a satisfactory growth rate, optimization of sucAB gene expression by randomizing the consensus "−35" region of the $P_{tac}$* promoter will result in a decrease in transcription initiation efficiency, as compared with $P_{tac}$* promoter, and as a consequence, a decrease in α-ketoglutarate dehydrogenase activity and an increase of the L-glutamic acid yield.

Example 3

Preparation of Artificial Regulatory Element Containing a Randomized Region, and Substitution of the Native Upstream Region of the sucAB-Genes with the Artificial Element in E. coli Chromosome A set of artificial regulatory elements containing a randomized "−35" region was obtained by PCR using synthesized primers P1 (SEQ ID NO: 2) and PS (SEQ ID NO: 10) and template plasmid pDR540. Primer PS (SEQ ID NO: 10) has 51 nucleotides and has a region with 4 random nucleotides, depicted in SEQ ID NO: 10 by the letter "n". The resulting artificial DNA fragments contained the hybrid regulatory element with the randomized region and the chloramphenicol resistance gene ($Cm^R$). Integration of this fragment into the chromosome was conducted as described in Example 1.

Colonies of the resulting integrants grown on the L-agar had a different size and growth rate. Selection was based on L-glutamic acid production. The two best clones, No. 2 and No. 21, were selected since they each had the highest level of L-glutamic acid production. These clones also exhibited a high level of total conversion of carbon from glucose into the amino acids of L-glutamic acid family, for example L-glutamic acid and L-proline. Genomic DNA from these clones was isolated using Genomic DNA isolation kit (Sigma, USA) according to the manufacturer's recommendations. To amplify the artificial regulatory element containing the randomized region, PCR was performed using the isolated DNA as a template and primers P1 (SEQ NO: 2) and P4 (SEQ ID NO:5). Sequences of both amplification products were determined by the Sanger method. Artificial promoters of clones 2 and 21 were designated as $P_{tac-2}$ and $P_{tac-21}$, respectively. Sequence of tetramers obtained by randomization are AGAT and TTGC, respectively.

Example 4

Influence of Artificial Regulatory Element on α-ketoglutarate Dehydrogenase Activity and L-glutamic Acid and L-proline Production Fermentation of clone 2 and 21, measurement of the L-glutamic acid and L-proline amounts, and determination of α-ketoglutarate dehydrogenase activity was performed as described in Example 2.

From the data in Table 1, it was hypothesized that the insertion of the tac-like constitutive promoters with optimized strength in place of the weaker native $P_{suc}$ could help in selecting variants of the strain which has improved L-glutamic acid production and a total conversion of carbon from glucose into the amino acids of L-glutamic acid family, for example, L-glutamic acid and L-proline. Moreover, the variants of the strain should preferably possess the ability to grow well on minimal media, while containing no additional supplements such as succinic acid, lysine or methionine, and with glucose as the carbon source. As seen in Table 1, the achieved optical densities of culture under standard fermentation conditions for the selected strains containing the $P_{tac-2}$ or $P_{tac-21}$ promoters were only slightly lower than for the strain containing the wild-type $P_{suc}$ promoter region.

tion 2002116773). The resulting strain 57leuA*ilvE⁻/pACYC-tyrB produces about 9 g/l of L-leucine in test tube fermentation.

$P_{tac-21}$ promoter was introduced into the chromosome of the obtained strain 57leuA*ilvE⁻/pACYC-tyrB by the standard procedure of P1 transduction. The L-leucine production

TABLE 1

| Strain | Promoter | SucAB activity, relative units | OD$_{540}$ | Cultivation time, hours | L-proline, g/l | L-glutamic acid, g/l | Total yield of L-glutamic acid family from glucose*, % |
|---|---|---|---|---|---|---|---|
| 702ilvA [pAYCTER1-cpg] | $P_{suc}$ | 90 | 37.8 | 25.5 | 18.0 | 8.1 | 37.3 |
| 702ilvA tac* [pAYCTER1-cpg] | $P_{tac}$* | 300 | 41.4 | 27.1 | 21.1 | 0 | 33.8 |
| 2 | $P_{tac-2}$ | 80 | 33.0 | 26.3 | 14.0 | 20.5 | 44.1 |
| 21 | $P_{tac-21}$ | 55 | 33.0 | 27.0 | 12.5 | 25.2 | 46.5 |

*The yield was calculated in terms of amount of L-glutamic acid, taking into account the molecular weights (MW) of L-glutamic acid and L-proline as follows: Total yield (%) = amount of L-glutamic acid * 100/amount of glucose + (amount of L-proline * MW of L-glutamic acid * 100)/(amount of glucose * MW of L-proline)

Example 5

Influence of Artificial $P_{tac-21}$ on α-ketoglutarate Dehydrogenase Activity and L-leucine Production As seen in Table 1, the artificial promoter $P_{tac-21}$ provides the lowest α-ketoglutarate dehydrogenase activity, and therefore, results in the best L-glutamic acid production. The decreased activity of SucAB enzyme, which is involved in the TCA cycle, reduces consumption of Acetyl-CoA in the TCA cycle. Acetyl-CoA is a precursor of L-leucine, so altered pool of Acetyl-CoA could be used for L-leucine biosynthesis and, consequently, might positively affect L-leucine production.

To support that hypothesis, the artificial $P_{tac-21}$ promoter of sucAB genes was transduced into an L-leucine producing E. coli strain to Cm resistance by the standard procedure of P1 transduction (Sambrook et al, "Molecular Cloning A Laboratory Manual, Second Edition", Cold Spring Harbor Laboratory Press (1989)), using E. coli strain 21 as a donor. Since the effect of altering L-leucine production could be seen only in an efficient L-leucine producer, L-leucine producing E. coli strain 57 (VKPM B-7386, Russian patent No. 2140450) productivity was further improved. Strain 57 produces 1.5-1.7 g/l of L-leucine in test tube fermentation. For that purpose, leucine auxotrophy was transduced by P1 phage from E. coli strain C600 (leu⁻) (Appleyard R. K., Genetics, 39, 440-452 (1954)) into the chromosome of strain 57, as described above. Then, the obtained leucine deficiency in strain 57leu⁻ was complemented by the same P1 transduction by leuA*BCD genes from donor E. coli strain 55. The strain 55 carries the leuA* gene, which encodes mutant alpha-isopropylmalate synthase free from feed-back inhibition by leucine (Russian patent No. 2201454). After the ilvE gene encoding activity of the branched chain amino acids transaminase was inactivated in the resulting strain 57leuA* and activity of the aromatic amino acid transaminase encoded by tyrB was enhanced in strain 57leuA*ilvE⁻ by transformation with recombinant plasmid pACYC-tyrB (Russian patent applicaby the obtained 57sucleuA*ilvE⁻/pACYC-tyrB strain has increased up to 11.4 g/l of L-leucine in test tubes fermentation.

A full loop of each strain 57leuA*ilvE⁻/pACYC-tyrB and 57suc leuA*ilvE⁻/pACYC-tyrB from the plate with L-agar was inoculated into 20×200 mm test tubes containing 2 ml medium containing 60 g/l glucose, 15 g/l (NH$_4$)$_2$SO$_4$, 1.5 g/l KH$_2$PO$_4$, 1 g/l MgSO$_4$*7H$_2$O, 0.1 g/l thiamine*HCl, 2 g/l CaCO$_3$, and incubated for 72 h at 34° C. with agitation (the rotation speed—250 rpm).

The amount of L-leucine was measured by high performance liquid chromatography (HPLC). Conditions for HPLC: Separon SGX C$_{18}$, 150×3.3 mm, 5 mkm, temp: 22° C. Eluent: CH$_3$CN—15% (v/v), Cu(CH$_3$COO)$_2$—0.1M. Flow rate—0.3 ml/mm, injection volume 0.5 μl. Detection at 232 nm.

As seen in Table 2, the substitution of the native promoter with the artificial $P_{tac-21}$ promoter into the chromosome of strain 57suc leuA*ilvE⁻pACYC-tyrB results in a decrease of ketoglutarate dehydrogenase activity and to improvement of L-leucine production.

TABLE 2

| Strain | Promoter | SucAB activity, relative units | Amount of L-leucine, g/l |
|---|---|---|---|
| 57leuA * ilvE⁻/pACYC-tyrB | Native $P_{suc}$ | 90 | 9.1 |
| 57leuA * ilvE⁻ suc/pACYC-tyrB | $P_{tac-21}$ | 36 | 11.4 |

While the invention has been described with reference to preferred embodiments thereof, it will be apparent to one skilled in the art that various changes can be made, and equivalents employed, without departing from the scope of the invention. All the cited references herein, including the foreign priority documents, RU 2003136412 and RU 2003106551, are incorporated as a part of this application by reference in its entirety.

INDUSTRIAL APPLICABILITY

According to the present invention, a bacterium having an optimized level of gene expression useful for amino acids or nucleic acid production, and a method for producing L-amino acids or nucleic acids using the bacterium are provided. The present invention is useful in the fermentation industry.

The invention claimed is:

1. An L-amino acid-producing *E. coil* comprising an optimized level of expression of the sucAB gene, and wherein said *E. coli* has an ability to produce an L-amino acid in greater amounts than a parental strain, and wherein the −35 region of a promoter for the sucAB gene on a chromosome in said *E. coli* comprises the sequence shown in SEQ ID NO: 10, wherein NNNN is AGAT or TTGC, and wherein the optimized expression is increased expression.

2. A method for producing an L-amino acid comprising (1) cultivating the *E. coli* according to claim 1 in a culture medium, and (2) collecting an L-amino acid from the culture medium.

3. The method according to claim 2, wherein said L-amino acid is selected from the group consisting of L-glutamic acid, L-glutamine, L-proline, L-arginine, and L-leucine.

* * * * *

SEQUENCE LISTING

<160> NUMBER OF SEQ ID NOS: 10

<210> SEQ ID NO 1
<211> LENGTH: 352
<212> TYPE: DNA
<213> ORGANISM: Escherichia coli

<400> SEQUENCE: 1

```
tgcaacgtaa tgcgtaaacc gtaggcctga taagacgcgc aagcgtcgca tcaggcaacc      60
agtgccgaat gcggcgtgaa cgccttatcc ggcctacaag tcattacccg taggcctgat     120
aagcgcagcg catcaggcgt aacaaagaaa tgcaggaaat ctttaaaaac tgccctgaca     180
ctaagacagt ttttaaaggt tccttcgcga gccactacg agacaagagc tcgcaagtga     240
accccggcac gcacatcact gtgcgtggta gtatccacgg cgaagtaagc ataaaaaaga     300
tgcttaaggg atcacgatgc agaacagcgc tttgaaagcc tggttggact ct             352
```

<210> SEQ ID NO 2
<211> LENGTH: 69
<212> TYPE: DNA
<213> ORGANISM: Artificial Sequence
<220> FEATURE:
<223> OTHER INFORMATION: Description of Artificial Sequence: primer

<400> SEQUENCE: 2

```
agagtccaac caggctttca aagcgctgtt ctgcatagct gtttcctcgc tcacaattcc      60
acacattat                                                              69
```

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 3

```
gcttaggtac cagatctccc tgttgacaat taatcatcgg                            40
```

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 4

```
tagcgagatc tctgatgtcc ggcggtgctt ttg                                   33
```

<210> SEQ ID NO 5
<211> LENGTH: 57
<212> TYPE: DNA
<213> ORGANISM: Artificial Sequence
<220> FEATURE:
<223> OTHER INFORMATION: Description of Artificial Sequence: primer

<400> SEQUENCE: 5

```
tgcaacgtaa tgcgtaaacc gtaggcctga taagacttac gccccgccct gccactc        57
```

```
<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 6
gaccatagat ctgaattcga gctcggtac                                    29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 7
acggccagat ctaagcttgc atgcctgca                                    29

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 8
aacagtgatc atttgcctgg cggcagtagc gcgg                              34

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 9
ataaaaagct tagatctcaa aaagagtttg tagaaacgca a                      41

<210> SEQ ID NO 10
<211> LENGTH: 51
<212> TYPE: DNA
<213> ORGANISM: Artificial Sequence
<220> FEATURE:
<221> NAME/KEY: n at positions 24-27
<222> LOCATION: n is any nucleotide
<223> OTHER INFORMATION: Description of Artificial Sequence: primer

<400> SEQUENCE: 10
gcttaggtac cagatctccc tgtnnnnaat taatcatcgg ctcgtataat g           51
```